United States Patent [19]
Dupont et al.

[11] Patent Number: 4,710,457
[45] Date of Patent: Dec. 1, 1987

[54] MONOCLONAL ANTIBODY FOR HUMAN HEMATOPOIETIC GLYCOPROTEINS AND METHOD

[75] Inventors: Bo Dupont, South Glenfield Harrison, N.J.; Yasuo Morishima, Nagoya, Japan; Nancy Collins, Larchmont, N.Y.; Shun-ichiro Ogata, Kagoshima, Japan; Kenneth O. Lloyd, Bronx, N.Y.

[73] Assignee: Sloan-Kettering Institute for Cancer Research, New York, N.Y.

[21] Appl. No.: 509,201

[22] Filed: Jun. 29, 1983

[51] Int. Cl.$^4$ .................. G01N 33/53; G01N 33/577; C12P 37/00
[52] U.S. Cl. .......................................... 435/7; 435/43; 435/68; 435/172.2; 435/240.27; 435/948; 530/387; 935/84; 935/95; 935/99; 935/100; 935/101; 935/103; 935/104; 935/105; 935/106; 935/108; 424/85; 424/86; 424/87
[58] Field of Search ................ 260/112 B; 424/85, 86, 424/87; 435/7, 43, 68, 172.2, 240, 241, 948; 935/89, 95, 99, 100, 101, 103, 104, 105, 106, 108; 530/387

[56] References Cited
FOREIGN PATENT DOCUMENTS
WO82/01192 4/1982 PCT Int'l Appl. .

OTHER PUBLICATIONS
Omary et al, J. Exp. Med., vol. 152, Oct. 1980, pp. 842–852.
Marishima et al, Immunogenetics, vol. 85, 529–535, 1982.

Primary Examiner—Christine M. Nucker
Attorney, Agent, or Firm—John P. White

[57] ABSTRACT

This invention concerns a new monoclonal antibody (mAb) 4C, recognizing a specific antigen, Leu 200, found in human hematopoietic tissues. The monoclonal antibody precipitates a series of glycoproteins (Leu 200) with a molecular weight range of about 190,000 to 230,000 from both T- and B-cell lines. The series of glycoproteins resolves into four discrete glycoprotein bands, the distribution of which varies according to the cell lines. Bands 3 and 4 predominate in a majority of T-cells whereas band 2 predominates in B cells. Thus, a Leu 200 antigen subset distribution is possible with mAb 4C. Bands 1, 2, 3, 4 have apparent molecular weights of 230K, 215K, 205K, and 190K respectively, with differences in their carbohydrate moieties. mAb 4C is a IgG sub two a, kappa immunoglobulin. 4C has potential use in leukemia, hematopoietic cell differentiation and transplantation diagnoses and therapy.

4 Claims, No Drawings

MONOCLONAL ANTIBODY FOR HUMAN HEMATOPOIETIC GLYCOPROTEINS AND METHOD

This invention was made with government support under NCI-CA-08748, CA-22507, CA-19267, CA-21445 and CA-23766 awarded by the U.S. Public Health Services, National Institutes of Health and NIAID grant AI 15227 and contract AI-82550. The government has certain rights in this invention This invention concerns a new monoclonal antibody (mAb) 4C, recognizing a specific antigen, Leu 200 restricted to human hematopoietic tissues. The monoclonal antibody precipitates a series of glycoproteins (Leu 200) with a molecular weight range of about 190,000 to 230,000 from both T- and B-cell lines. The series of glycoproteins resolves into four discrete glycoprotein bands, the distribution of which varies according to the cell line. Bands 3 and 4 predominate in a majority of T-cells whereas band 2 predominates in B cells. Thus, a Leu 200 antigen subset distribution is possible with mAb 4C. Bands 1, 2, 3, 4 have apparant molecular weight of 230K, 215K, 205K and 190K respectively with differences in their carbohydrate moieties. mAb 4C is a IgG sub two a, kappa immunoglobulin.

In 1975 Köhler and Millstein introduced a procedure for the production of monoclonal antibodies (mAbs) using hybrid cells (hybridomas) which allows the production of almost unlimited quantities of antibodies of precise and reproducible specificity. Conventional antisera, produced by immunizing animals with tumor cells or other antigens, contain a myriad of different antibodies differing in their specificity and properties, whereas hybridomas produce a single antibody with uniform characteristics. The Köhler-Millstein procedure entails the fusion of spleen cells from an immunized animal with an immortal myeloma cell line. From the fused cells (hybridomas), clones are selected that produce antibody of the desired specificity. Each clone continues to produce only that one antibody. As hybridoma cells can be cultured indefinitely (or stored frozen in liquid nitrogen), a constant supply of antibody is assured.

Antibodies are proteins that have the ability to combined with and recognize other molecules, known as antigens. Monoclonal antibodies are no different from other antibodies except that they are very uniform in their properties and recognize only one antigen or a portion of an antigen known as a determinant.

In the case of cells, the determinant recognized is an antigen on or in the cell which reacts with the antibody. It is through these cell antigens that a particular antibody recognizes, i.e. reacts with, a particular kind of cell. Thus the cell antigens are markers by which the cell is identified.

These antigenic markers may be used to observe the normal process of cell differentiation and to locate abnormalities within a given cell system. The process of differentiation is accompanied by changes in the cell surface antigenic phenotype, and antigens that distinguish cells belonging to distinct differentiation lineages or distinguish cells at different phases in the same differentiation lineage may be observed if the correct antibody is available.

The preparation of hybrid cell lines can be successful or not depending on such experimental factors as nature of the innoculant, cell growth conditions, hybridization conditions etc. Thus it is not always possible to predict successful hybridoma preparation of one cell line although success may have been achieved with another cell line.

Progress in defining surface antigens on melanocytes was made possible by the recently discovered technique of culturing melanocytes from normal skin (Eisinger, et al., Proc. Nat'l. Acad. Sci. USA, 79 2018 (March 1982). This method provides a renewable source of proliferating cells for the analysis of melanocyte differentiation antigens. Likewise, a large number of cell lines derived from melanomas have now been established and these have facilitated the analysis of melanoma surface antigens. The advent of mAbs has greatly accelerated knowledge about the surface antigens of malignant melanoma. Cells markers on both melanomas and melanocytes have been identified. A panel of typing monoclonal antibodies has been selected which recognizes differentiation antigen characteristics at each stage of development in both melanocytes and melanomas. These differentiation antigens may be used to classify melanocytes and melanomas and to group them into characteristic sub-sets. Dippold et al. *Proc. Nat'l. Acad. Sci. U.S.A.* 77, 6114 (1980) and Houghton, et al. *J. Exp. Med.* 156, 1755 (1982). Immunoassay of melanocytes and melanoma cells within sub-sets is thus made possible.

Initial recognition of differentiation antigens cam about through analysis of surface antigens of T-cell leukemias of the mouse and the description of the TL, Thy-1, and Lyt series of antigens. (Old, Lloyd J., Cancer Research, 41, 361–375, February 1981) The analysis of these T-cell differentiation antigens was greatly simplified by the availability of normal T cells and B cells of mouse and man. (See U.S. Pat. Nos. #4,361,549-559; #4,364,932-37 and 4,363,799 concerning mAb to Human T-cell antigens).

A group of high molecular weight cell-surface glycoproteins characteristic of hematopoietic cells has been described in mice [Trowbridge et al. *Proc. Nat'l. Acad. Sci. U.S.A.* 72:157 (1975)], rats [Fabre and Williams *Transplantation* 23:349 (1977)], and humans [Omary et al. *J. Exp. Med* 152:842 (1980)], Dalchau et al. [*Eur. J. Immunology* 10:737 (1980)]. Different subsets of lymphocytes express different forms of these antigens [Trowbridge et al. *J. Exp. Med.* 148:313 (1978), Hoessli and Vassalli *J. Immunol* 125:1758 (1980)]. These families of glycoproteins have been analyzed biochemically [Trowbridge et al. Supra 1975, Trowbridge et al. Supra 1976, Andersson and Gahmberg, *Blood* 52:57 (1978)] and by the precipitation of specific components with xenogeneic antisera [Fabre and Williams Supra 1977, Hoessli and Vassalli Supra 1980, Andersson and Metzger *J. Immunol.* 120:262 (1978), Niaudet and Greaves *J. Immunol.* 124:1203 (1980)] and with mouse monoclonal antibodies [Trowbridge Supra 1978, Omary et al. Supra 1980, Dalchau et al. Supra 1980, Dalchau and Fabre *J. Exp. Med.* 153:753 (1981), Coffman and Weissman *Nature* 289:681 (1981)]. In these studies, the major high molecular-weight glycoproteins of B-lymphocytes and B-cell lines were found to be larger than the corresponding components of T-lymphocytes and T-cell lines [Trowbridge Supra 1978. Sunderland et al. *Eur. J. Immunol,* 9:155, 1979, Omary et al. Supra, 1980, Hoessli and Vassalli Supra 1980, Dunlap. et al. J. Immunol. 125:1829 (1980), Coffman and Weissman Supra 1981, Berger et al. Hum. Immunol.

3:231 (1981)]. The high and low molecular weight species are, however, considered to be related, as antibodies to one population react with the other. Also, peptide maps generated from immunoprecipitated glycoproteins from B- and T-cells have been shown to be very similar or identical [Omary et al. Supra (1980), Dunlap et al. Supra (1980)]. In general, however, the high molecular weight forms (200-220 kd) were considered to be characteristic of B-cells whereas the lower molecular weight species (170-200 kd) predominated in T-cells.

We now analyze the high molecular-weight glycoproteins of human hematopoietic cells using a new mouse monoclonal antibody (mAb 4C). mAb 4C is produced by the hybridoma method of Köhler and Millstein [Nature 256:495 (1975)] after the immunization of BALB/c mice with phytohemagglutinin-stimulated human peripheral T-lymphocytes. As shown in Table 1 below, serological analysis using indirect immunofluorescence and absorption studies demonstrates that the antigen (Leu 200), detected by mAb 4C, is restricted to hematopoietic tissues and is expressed on all peripheral lymphocytes, monocytes, granulocytes, a majority of thymocytes, spleen cells, and bone marrow cells.

TABLE 1

Tissue distribution of Leu-200 tested by indirect immunofluorescence and/or absorption test

| Positive | Negative |
|---|---|
| | Normal tissues from: |
| Peripheral blood lymphocytes* (99) | |
| Peripheral blood monocytes* (99) | Red blood cells* |
| Peripheral blood granulocytes* (99) | brain** |
| Thymocytes* (96) | liver** |
| Spleen mononuclear cells* ** (86) | kidney** |
| Bone marrow mononuclear, cells* (86) | heart |
| | Tumor cell lines** from: |
| T lymphoblastoid cell lines* (86-100) (82) (CCRF-CEM, 45, RPMI-8042, HSB-2, MOLT-4) | brain (BZ, AJ), bladder (J-24, bone (U-20S), colon (SW-1221) |
| B lymphoblastoid cell lines* (31-98) (DAUDI**, SB, PB-1, WALK-1) | kidney (SK-RC-7,18), liver (SK-HEP-1) lung (SK-LC-LL), melanoma (SK-MEL-29,37) |
| Erythro-leukemia cell line* (K562) (90) | Cervix (ME-180) |
| Monocytic cell line* (U937) (98) | |

*Marked cells were tested by indirect immunofluorescence, and numbers in bracket are % positive cells. Two million cells were incubated with 0.05 ml of mAb 4C (1:20 dilution of supernatant) at 4C for 30 min. After washing twice, 0.05 ml flourescein-conjugated goat anti-mouse IgG (1:10 dilution) were added and incubated for another 30 min. at 4C.
**Marked cells or tissues were tested by absorption test. Packed cells (0.05 ml) from normal tissue and in vitro cultured cell lines of hematopoietic and non hematopoietic origin were suspended in an equal volume of mAb 4C (1:20 dilution of supernantant) and incubated for 1 h at 4° C. Remaining antibody was then determined using C'-microcytotoxicity tests.

By FACS IV analysis, T-cells, non-T-cells, and monocytes show similar patterns of immunofluorescent histograms, while granulocytes show weaker intensity of immunofluorescence, and thymocytes have populations with both strong and weak intensities of immunofluorescence. In the complement dependent microcytotoxicity test (NIH standard method, mAb 4C ($IgG_{2a}$ kappa immunoglobulin) kill nearly 100% of both T- and non-T cells at 1:125 dilutions. C-cytotoxicity to monocytes is the same as that to lymphocytes, but granulocytes are less efficiently killed.

Immunoprecipitations of NP-40 extracts of [$^3$H]-GlcN-labeled human T- and B-cell lines are carried out with mAb 4C and the precipitates are analyzed by SDS-PAGE as described elsewhere (Ueda et al. Proc. Nat'l. Acad. Sci. U.S.A. 78:5122 1981) described below.

Example of Immunoprecipitation Procedures

Cells were metabolically labeled with [$^3$H]glucosamine in complete Eagle's medium containing 15 micro Ci of [$^3$H]glucosamine (New England Nuclear; 30–60 Ci/mmol; 1 Ci=$3.7 \times 10^{10}$ becquerels) per ml for 48 hr at 37° C.; the labeled cells were extracted with 0.5% Nonidet P-40 (NP-40) in Tris buffer as described Ogata, S. et al. Proc. Nat'l. Acad. Sci. U.S.A. 78:770 (1981) except that the 3 M KCl treatment was omitted. Immunoprecipitation was carried out by mixing a portion of the cell extract ($1 \times 10^5$ cpm) with 2 microliter of mouse serum and 20 microliters of rabbit anti-mouse Ig serum (Cappel Laboratories, Cochranville, Pa.) in Tris buffer. Immune complexes were isolated by using Staphylococcus aureus and analyzed by $NaDodSO_4$/polyacrylamide gel electrophoresis [SDS-PAGE] as described [Dippold et al. Supra, Bonner and Laskey, Eur. J. Biochem. 46, 83 (1974)] wherein SDS=NaDodS04=sodium dodecylculfate. [$^{35}$S]Methionine-labeled samples were sodium dodecylsulfate. immunoprecipitated in a similar manner, except that Sepharose-rabbit F(ab')$_2$ anti-mouse IgG was used for isolating the complexes. To determine the pI of the antigens, immunoprecipitates were examined by two-dimensional electrophoresis by the O'Farrell procedure [J. Biol. Chem. 250:4007 (1975)], modified as described Ogata, Supra.

This procedure is applied to T- and B- cells as examples. The examples with respect to specific T- and B-cell lines are for illustrative purposes only and are not meant to limit the invention to said examples. Other T- and B-cell lines as well as other hematopoietic cell lines can be used to not only produce this type of mAb but serve as well as target cell for mAb 4C.

Table 2. (below) illustrates the distribution of Leu 200 slycoprotein bands 1, 2, 3, and 4 (apparent molecular weights 230K, 215K, 205K, 190K, respectively) amont five T-cell lines and eight B-cell lies. Four T-cell lines out of the five analyzed, had bands 3 and 4 as major components whereas seven C-cell lines out of the eight examined, had band 2 as a major glycoprotien with bands 3 and 4 as minor components.

TABLE 2

Distribution of Leu 200 Bands 1, 2, 3, and 4 in T- and B-cells

| T-CELL LINES: | | HSB | CEM | 45 | MOLT 4 | 8402 | |
|---|---|---|---|---|---|---|---|
| 1 | 230K | | | Minor(1) | | | |
| 2 | 215K | | | Major | | | |
| 3 | 205K | Minor(1) | Minor(1) | Minor(2) | Minor(1) | Minor(1) | |
| 4 | 190K | Major | Major | | Major | Major | |

| B-CELL LINES: | | SB | DAUDI | FBIB | GERBER | FS-2 | WT-52 | REMB | WALK |
|---|---|---|---|---|---|---|---|---|---|
| 1 | 230K | | | Major | | | | | |
| 2 | 215K | Major | Major | | Major | Major | Major | Major | Minor(2) |
| 3 | 205K | Minor(1) | Minor(2) | | Minor(2) | Minor(1) | Minor(1) | Minor(1) | Minor(2) |

TABLE 2-continued

| | | | | | | | | |
|---|---|---|---|---|---|---|---|---|
| \multicolumn{9}{c}{Distribution of Leu 200 Bands 1, 2, 3, and 4 in T- and B-cells} |
| 4 | 190K | Minor(1) | Minor(2) | | Minor(2) | Minor(2) | Minor(2) | Major |

Legend to Table 2. Illustration of Leu 200 glycoproteins present in various human B- and T-cell lines. The apparent molecular weight of the various bands are given in thousands (K). The minor bands are represented as minor(1) and minor(2) where minor(1) is a heavier band than minor(2).

These lower molecular weight components are probably not biosynthetic precusors of band 2 (as was found in the Ly-5 system, Watson et al. *J. Immunol.* 127:38 1981) since after 40 h of incubation with [$^3$H]-GlcN, all the labeled sugar would be present in biosynthetically completed products (Lloyd et al. *J. Immunol.* 126:2408 1981). One T-cell line (45), however, expresses band 2 as a major component, and one B-cell line (WALK-1) expresses band 4 as a major constituent. Another B-cell line (FBIB) gives only one band, the molecular weight of which is a little higher than band 2. When the immunoprecipitates are analyzed on 9% acrylamide gels, bands 3 and 4 fuse to form a single but rather diffuse band. Thus, on 9% acrylamide gels, T-cell lines usually give a single band of 200,000 daltons while B-cell lines show a band of 220,000 daltons as the major glycoprotein. Such observations were the basis for the proposed differences in high molecular weight glycoproteins of human T- and B-cells (Omary et al. Supra 1980, Sunderland et al. Supra 1979, Hoessli and Vassalli Supra 1980, Dunlap et al. Supra 1980). In this study we show that at least one B-cell line and one T-cell line do not show a characteristic glycoprotein band. On the contrary, a B-cell line (WALK-1) expresses a band also expressed by T-cell lines and a T-cell line (45) has a band expressed by B-cell lines. It would appear, therefore, that the presence of the higher molecular weight species of the Leu 200 family is not invariably a characteristic of B-cell lines nor are T-cell lines always characterized by the lower molecular weight members of the family.

A number of investigators (Hoessli and Vassali Supra 1980, Dunlap et al. Supra 1980. Coffman and Weissman Supra 1981) have suggested that since the 220 000 and 200 000 dalton glycoproteins of B- and T-cells have very similar or identical peptide maps, their different mobilities in SDS-PAGE and their different antigenic properties may be due to differences in the number, size and/or composition of their carbohydrate moieties. We present direct evidence for such a difference in the carbohydrate moieties of the high and low molecular weight members of the Leu 200 complex. This information is obtained by determining the effect of neuraminidase digestion of Leu 200 glycoproteins from both T- and B-cells. NP-40 extracts ($9 \times 10^5$ cpm) are incubated with neuraminadase (25 U) at 37° for 8 hours before immunoprecipitation with mAb 4C.

Neuraminidase treatment of the glycoproteins from cell lines carrying bands 3 and 4 resulted in an increased mobility of these components on SDS-PAGE. Similar treatment of glycoproteins from cells having bands bands 1 and 2 as their major components did not result in any detectable alternation in the mobility of these glycoproteins. It should be noted that the susceptibility to neuraminidase was not a characteristic of T-cell lines in general but rather of the preferential expression of the lower molecular weight (bands 3 and 4) glycoprotein in a particular cell line.

In order to study the carbohydrate moieties of Leu 200 glycoproteins, immunoprecipitated samples are treated with mild alkaline borohydride under conditions that release both N- and O-linked chains, and the released oligosacchardies are analyzed by gel filtration (Ogata and Lloyd, Procedings VIth International Symposium on Glycoconjugates, Tokyo, Japan Sept. 20–25 p. 23, 1981). [$^3$H]-GlcN-labeled glycoproteins precipitated by mAb 4C and absorbed on *S. aureus* were treated with 0.4 ml of 0.05 M NaOH containing 1.0 M NaBH$_4$. The supernatant solution was heated at 50° for 15 h and then adjusted to pH 5.0 with acetic acid. Oligosaccharides were analyzed by Sephadex G-50 column chromatography in 0.1 M pyridine acetate pH 5.7 buffer as described previously (Ogata and Lloyd Supra 1981). Five cell lines (3T-cell and 2 B-cell lines) yield peaks that are eluted at positions corresponding to a molecular weight of about 2600 and that probably represent complex-type carbohydrate chains. A B-cell line (DAUDI) gave a peak with a slightly lower molecular weight (approximately 2300). Except for a T-cell line (45), the carbohydrate chains of Leu 200 glycoproteins from all the cell lines analyzed change their elution profiles (to a lower molecular weight region) after neuraminidase treatment. This change is small but is consistent with the expected sialic content of oligosaccharide chains. The data indicate that even the glycoproteins of Leu 200 derived from B-cell lines, which do not show any apparent shift of mobility on SDS-PAGE after neuraminidase treatment, contain sialic acid residues in their carbohydrate structures. The demonstration by other workers (Andersson and Gahmberg Supra 1978, Dalchau and Fabre Supra 1981) that the 220 000 dalton glycoproteins are labeled by periodate-borotritiide treatment is also consistent with this conclusion.

Our results indicate that bands 3 and 4 from both B-and T-cells have a higher sialic acid content than bands 1 and 2, such that removal of sialic acid results in a relatively large and detectable change in their mobility on SDS-PAGE analysis. This difference may arise from either a higher degree of glycosylation in bands 3 and 4, or from all Leu 200 species having equal numbers of carbohydrate chains but with bands 3 and 4 having different (e.g.,, more branched) carbohydrate structures that would result in a higher degree of sialylation. Recently, Childs and Feizi *Biochem. Biophys. Res. Commun.* 102:1158 (1981) demonstrated differences in the reactivity of the high molecular weight glycoproteins of B- and T- human lymphocytes with I and i blood group-specific antibodies. A direct comparison with our data is difficult because of the different techniques used, and because the components were not identified as belonging to the Leu 200 family using a specific antibody.

These glycosylation differences could explain the specificity of antibodies that preferentially detect the 220 000 dalton component (Dalchau and Fabre Supra 1981) in that the determinants detected by these antibodies could be masked by glycosylation in the glycoproteins with lower apparent molecular weights. An alternative explanation is, of course, that such antibodies could be directed against carbohydrate determinants on the particular Leu-200 species. Such carbohydrate differences may also explain some of the biological properties of lymphoid cells. For instance, they could determine cell-cell interactions between lymphocytes or with other cell or they may be related to the differentiation state of a particular lymphocyte subset. Antibody 4C could be used for diagnosis and/or immunotherapy against diseased hematopoietic cells as for instance, in leukemia, or in disease where hematopoietic cells are involved or can be used or markers for the disease. Hematopoietic specimens can be diagnosed and treated. 4C has potential use in transplantation as for example, use of mAb 4C or a modified version of 4C (perhaps cross-linked to toxin etc.), to deplete bone marrow lymphocytes and reduce graft versus host disease in bone marrow transplantation patients.

Monoclonal antibody 4C is on deposit and available at Sloan-Kettering Institute, Human Immunogenetics Section, Department of Clinical Immunology, 1275 York Avenue, New York, N.Y. 10021.

4C has been deposited with the American Type Culture Collection (ATCC), 12301 Parklawn Drive, Rockville, Md. 20852 on June 28, 1983 and has been given an ATCC accession number of HB 8311.

What is claimed:

1. Method for differentiating between human B cells and T cells in a human hematopoietic specimen which comprises (a) contacting the human hematopoietic specimen with monoclonal antibody 4C (ATCC Accession No. HB 8311) under immunoprecipitating conditions so as to allow the formation of 4C: Leu 200 glycoprotein immunoprecipitate complexes: (b) analyzing the immunoprecipitate complexes by SDS-PAGE to determine the presence of Leu 2 glycoproteins having molecular weights of approximately 230 kD, 215 kD, 205 kD and 190 kD; and (c) differentiating B cells from T cells wherein B cells are indicated when the 215 kD glycoprotein predominates in appearance over the 205 kD and 190 kD glycoproteins, are wherein T cells and indicated when the 205 kD and 190 kD glycoproteins predominate over the 215 kD glycoprotein.

2. Method of claim 1 wherein the hematopoietic specimen to be contacted with the monoclonal antibody is an NP-40 extract of -GlcN-labelled human hematopoietic specimen.

3. Method of claim 1 wherein the Leu 200 glycoproteins are treated with neuraminadase resulting in an increased electrophoretic mobility in the 205 kD and 190 kD glycoproteins relative to untreated material.

4. Method of claim 1 wherein the 205 kD and 190 kD glycoproteins have a higher sialic acid content relative to the 230 kD and 215 kD glycoproteins.

* * * * *